United States Patent [19]

Zinke et al.

[11] Patent Number: 5,362,419
[45] Date of Patent: Nov. 8, 1994

[54] DITHIOPHOSPHORIC ACID DERIVATIVES AS LUBRICANT ADDITIVES

[75] Inventors: Horst Zinke, Reichelsheim/Odw., Germany; Rolf Schumacher, Marly, Switzerland

[73] Assignee: Ciba-Geigy Corporation, Ardsley, N.Y.

[21] Appl. No.: 68,375

[22] Filed: May 27, 1993

[30] Foreign Application Priority Data

Jun. 2, 1992 [CH] Switzerland ............... 1772/92-2

[51] Int. Cl.$^5$ .......................................... C10M 137/10
[52] U.S. Cl. .................................. 252/46.6; 558/179
[58] Field of Search ........................ 252/46.6; 558/179

[56] References Cited

U.S. PATENT DOCUMENTS

| | | | |
|---|---|---|---|
| 3,350,348 | 10/1967 | Braid et al. | 252/46.6 |
| 3,591,666 | 7/1971 | Pellegrini et al. | 558/179 |
| 3,629,376 | 12/1971 | Regel et al. | 558/179 |
| 3,646,172 | 2/1972 | Myers | 252/46.6 |
| 3,689,605 | 9/1972 | Santi | 558/179 |
| 3,784,588 | 1/1974 | Miles | 252/46.6 |
| 4,333,841 | 6/1982 | Schmidt et al. | 558/179 |
| 4,387,095 | 6/1983 | Saito et al. | 558/179 |
| 4,435,338 | 3/1984 | Michaelis et al. | 252/46.6 |
| 4,544,492 | 10/1985 | Zinke et al. | 252/46.7 |
| 4,713,186 | 12/1987 | Kristen et al. | 252/30 |
| 4,917,809 | 4/1990 | Zinke et al. | 252/32.7 E |

FOREIGN PATENT DOCUMENTS

1287331 4/1973 United Kingdom .
1367663 9/1974 United Kingdom .

*Primary Examiner*—Ellen M. McAvoy
*Attorney, Agent, or Firm*—Michele A. Kovaleski; Luther A. R. Hall

[57] ABSTRACT

There are disclosed compounds of formula I

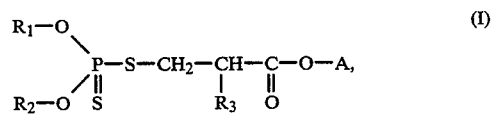

$R_1$ and $R_2$ are each independently of the other $C_3$-$C_{18}$alkyl, $C_5$-$C_{12}$cycloalkyl, $C_5$-$C_6$cycloalkylmethyl, $C_9$-$C_{10}$bicycloalkylmethyl, $C_9$-$C_{10}$tricycloalkylmethyl, phenyl, $C_7$-$C_6$alkylphenyl or, taken together, are

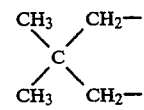

$R_3$ is hydrogen or methyl, A is

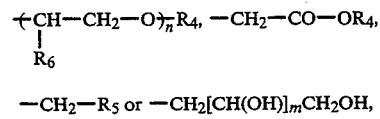

$-CH_2-R_5$ or $-CH_2[CH(OH)]_mCH_2OH$, $R_4$ is hydrogen or $C_1$-$C_6$alkyl, and
$R_5$ is a 5- or 6-membered saturated heterocyclic ring,
$R_6$ is hydrogen or methyl,
n is an integer from 1 to 11 and m is an integer from 0 to 4.

These compounds are particularly suitable for use as additives for lubricant compositions, hydraulic fluids and machining fluids.

8 Claims, No Drawings

DITHIOPHOSPHORIC ACID DERIVATIVES AS LUBRICANT ADDITIVES

The present invention relates to dithiophosphoric acid derivatives, to the use thereof as lubricant additives and to lubricating compositions, hydraulic fluids and machining fluids containing them.

It has been proposed to use (thio)phosphates in conjunction with solid lubricants such as graphite (EP-A-0 214 434).

High-temperature lubricant additives are also known, namely compounds of formula $(R^{IV}X)_nP(=Y)(ZR^V)_{3-n}$, wherein X, Y and Z are each independently of one another O or S and $R^{IV}$ and $R^V$ are $C_1$-$C_{12}$alkyl which may be interrupted by —O—, —S— or —CO—O— (EP-A-0 267 875).

The phosphorus-sulfur additives for lubricants which are currently predominant are zinc dialkyl dithiophosphates. However, state of the art combustion engines require ever more frequently lubricant additives of preferably low ash content, i.e. the metal content should be as low as possible.

Surprisingly, it has now been found that the compounds of formula I below, especially at low temperatures, afford very good antiwear protection. The compounds contain no zinc, i.e. they meet current requirements, are liquid, and thus are easy to handle in connection with lubricating compositions.

Accordingly, the invention relates to compounds of formula I $$\begin{array}{c} R_1-O \\ \phantom{R_1-}\diagdown \\ \phantom{R_1-O}P-S-CH_2-CH-C-O-A, \text{ wherein} \\ \phantom{R_1-}\diagup\|\phantom{P-S-CH_2-}|\phantom{-}\| \\ R_2-O\phantom{\diagup}S\phantom{P-S-CH_2-}R_3\phantom{-}O \end{array} \quad (I)$$

$R^1$ and $R_2$ are each independently of the other $C_3$-$C_{18}$alkyl, $C_5$-$C_{12}$cycloalkyl, $C_5$-$C_6$cycloalkylmethyl, $C_9$-$C_{10}$bicycloalkylmethyl, $C_9$-$C_{10}$tricycloalkylmethyl, phenyl, $C_7$-$C_{24}$alkylphenyl or, taken together, are $$\begin{array}{c} CH_3 \phantom{-} CH_2- \\ \diagdown \phantom{-} \diagup \\ C \\ \diagup \phantom{-} \diagdown \\ CH_3 \phantom{-} CH_2- \end{array},$$

$R_3$ is hydrogen or methyl, A is $$\text{(}CH-CH_2-O)_nR_4, -CH_2-CO-OR_4,$$
$$|$$
$$R_6$$

$$-CH_2-R_5 \text{ or } -CH_2[CH(OH)]_mCH_2OH,$$

$R_4$ is hydrogen or $C_1$-$C_6$alkyl, and
$R_5$ is a 5- or 6-membered saturated heterocyclic ring,
$R_6$ is hydrogen or methyl,
n is an integer from 1 to 11 and m is an integer from 0 to 4.

$R_1$ and $R_2$ defined in the above formulae as $C_3$-$C_{18}$alkyl are branched or unbranched radicals. Illustrative examples are propyl, isopropyl, n-butyl, isobutyl, tert-butyl, pentyl, isopentyl, hexyl, heptyl, 3-heptyl, octyl, 2-ethylhexyl, nonyl, decyl, undecyl, dodecyl, tridecyl, tetradecyl, pentadecyl, hexadecyl, heptadecyl, octadecyl, 2-ethylbutyl, 1-methylpentyl, 1,3-dimethylbutyl, 1,1,3,3-tetramethylbutyl, 1-methylhexyl, isoheptyl, 1-methylheptyl, 1,1,3-trimethylhexyl or 1-methylundecyl.

$R_1$ and $R_2$ defined as $C_5$-$C_{12}$cycloalkyl may typically be cyclopentyl, cyclohexyl, cycloheptyl, cyclooctyl or cyclododecyl. Cyclopentyl and cyclohexyl are preferred. Cyclohexyl is most preferred.

$R_1$ and $R_2$ defined as $C_5$-$C_6$cycloalkylmethyl will be taken to mean cyclopentylmethyl and, preferably, cyclohexylmethyl.

$R_1$ and $R_2$ defined as $C_9$-$C_{10}$cycloalkylmethyl are typically decalinylmethyl. $R_1$ and $R_2$ defined as $C_9$-$C_{10}$tricycloalkylmethyl are preferably a group of formula $R_5$ defined as a 5- or 6-membered heterocyclic ring may be piperidino, pyrrolidino, piperazino, morpholino, pyrimidino or tetrahydrofuryl, preferably 2-tetrahydrofuryl.

Preferred compounds are those wherein $R_1$ and $R_2$ are each independently of the other $C_3$-$C_{18}$alkyl, $C_5$-$C_6$cycloalkyl or $C_7$-$C_{18}$alkylphenyl, $R_5$ is tetrahydrofuryl, n is 1 to 6 and m is 0 to 2.

$R_1$ and $R_2$ are most preferably identical. $R_3$ is preferably hydrogen.

The invention further relates to compositions comprising a) a lubricant, a machining fluid or hydraulic fluid, and b) at least one compound of formula I, the compounds cited above as preferred resulting in preferred compositions.

The lubricants, machining fluids or hydraulic fluids contained in the inventive compositions can decompose readily to a greater or lesser degree under the action of heat, mechanical stress (especially induced by shear forces) and chemical reagents (especially atmospheric oxygen).

The compounds of formula I afford protection against such influences and will conveniently be present in the novel compositions in amounts of 0.01 to 10% by weight, typically 0.05 to 5% by weight, preferably 0.05 to 3% by weight and, most preferably, 0.1 to 2% by weight. The novel compositions may contain one or more than one of these compounds, and the percentages by weight are based on the total amount of said compounds. The basis of calculation is the total weight of the lubricant, machining fluid or hydraulic fluid without the compounds of formula I.

The invention thus also relates to the use of compounds of formula I as additives for lubricants, hydraulic fluids and machining fluids, especially as extreme-pressure and antiwear additives as well as friction modifiers.

Such a utility also entails a process for enhancing the performance properties of lubricants, hydraulic fluids and machining fluids. The novel utility also encompasses the protection of the metal parts to be lubricated against mechanical wear (antiwear protection).

The suitable lubricants, hydraulic fluids and machining fluids are typically based on mineral or synthetic oils or mixtures thereof. The lubricants are known to the skilled person and are described in the relevant literature, inter alia in Dieter Klamann, "Schmierstoffe und verwandte Produkte" (Lubricants and Related Products) (Verlag Chemie, Weinheim, 1982), in Schewe-Kobek, "Das Schmiermittel-Taschenbuch" (Handbook of Lubricants) (Dr. Alfred Htithig-Verlag, Heidelberg, 1974), and in "Ullmanns Enzyklopadie der technischen Chemie" (Ullmann's Encyclopedia of Industrial Chemistry), Vol. 13, pages 85–94 (Verlag Chemie, Weinheim, 1977).

The lubricants are preferably oils and fats are typically derived from a mineral oil. Oils are preferred.

A further group of lubricants suitable for use in the practice of this invention comprises vegetable or animal oils, fats, tallows and waxes or mixtures with one another or with the mineral or synthetic oils referred to above. Vegetable and animal oils, fats, tallows and waxes are typically palm nut oil, palm oil, olive oil, beet oil, rapeseed oil, linseed oil, ground nut oil, soybean oil, cottonseed oil, sunflower seed oil, pumpkin seed oil, coconut oil, corn oil, castor oil, walnut oil and mixtures thereof, fish oils, the tallows of slaughter animals, e.g. beef tallow, neat's foot and bone oil, as well as the modified, epoxidised and sulfoxidised forms thereof, typically epoxidised soybean oil.

The mineral oils are based in particular on hydrocarbon compounds.

Synthetic lubricants typically comprise lubricants based on aliphatic or aromatic carboxylates, polymeric esters, polyalkylene oxides, phosphates, poly-$\alpha$-olefins or silicones, on a diester of a divalent acid with a monohydric alcohol, typically dioctyl sebacate or dinonyl adipate, on a triester of trimethylolpropane with a monovalent acid or with a mixture of acids, conveniently trimethylolpropane tripelargonate, trimethylolpropane tricaprylate or mixtures thereof, on a tetraester of pentaerythritol with a monovalent acid or with a mixture of such acids, typically pentaerythritol tetracaprylate, or on a complex ester of monovalent and divalent acids with polyhydric alcohols, for example a complex ester of trimethylolpropane with caprylic and sebacic acid or of a mixture thereof. Especially suitable lubricants are, in addition to mineral oils, typically poly-$\alpha$-olefins, ester-based lubricants, phosphates, glycols, polyglycols and polyalkylene glycols and mixtures thereof with water.

Machining fluids and hydraulic fluids can be prepared from the same substances as those described above in connection with the lubricants. Often they are also emulsions of such substances in water or other liquids.

The lubricating compositions of this invention are used, inter alia, for combustion engines, typically for motor vehicles powered by engines of the Otto-cycle, diesel, two-stroke, Wankel or orbital type.

The compounds of formula I are readily soluble in lubricants, machining fluids and hydraulic fluids and are therefore especially suitable for use as additives for lubricants, machining fluids and hydraulic fluids. Their surprisingly good antiwear properties merit special mention.

The invention thus further relates to a process for enhancing the performance properties of lubricants, machining fluids and hydraulic fluids, which comprises adding thereto compounds of formula I.

The compounds of formula I can be blended with the lubricating compositions in a manner known per se. The compounds are, for example, readily soluble in oils. It is also possible to prepare a masterbatch, which can be diluted in accordance with consumption to suitable concentrations with the appropriate lubricant. In such cases, concentrations higher than 10% by weight are also possible.

The lubricants, machining fluids and hydraulic fluids of this invention may also contain other additives which are added for further enhancement of the basic properties. These further additives comprise antioxidants, metal deactivators, rust inhibitors, viscosity improvers, pour-point depressants, dispersants, detergents, other extreme-pressure and antiwear additives.

Illustrative examples of such further additives are:
Examples of phenolic antioxidants 1. Alkylated monophenols, for example 2,6-di-tert-butyl-4-methylphenol, 2-tert-butyl-4,6-dimethylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-($\alpha$-methylcyclohexyl)-4,6-dimethylphenol, 2,6-dioctadecyl-4-methylphenol, 2,4,6-tricyclohexylphenol, 2,6-di-tert-butyl-4-methoxymethylphenol, 2,6-dinonyl-4-methylphenol, 2,4-dimethyl-6-(1'-methylundec-1'-yl)phenol, 2,4-dimethyl-6-(1'-methylheptadec-1'-yl)phenol, 2,4'-dimethyl-6-(1'-methyltridec-1'-yl)phenol and mixtures thereof.

2. Alkylthiomethylphenols, for example 2,4-dioctylthiomethyl-6-tert-butylphenol, 2,4-di-octylthiomethyl-6-methylphenol, 2,4-dioctylthiomethyl-6-ethylphenol and 2,6-didodecylthiomethyl-4-nonylphenol.

3. Hydroquinones and alkylated hydroquinones, for example 2,6-di-tert-butyl-4-methoxyphenol, 2,5-di-tert-butylhydroquinone, 2,5-di-tert-amylhydroquinone, 2,6-diphenyl-4-octadecyloxyphenol, 2,6-di-tert-butylhydroquinone, 2,5-di-tert-butyl-4-hydroxyanisole, 3,5-di-tert-butyl-4-hydroxyanisole, 3,5-di-tert-butyl-4-hydroxyphenyl stearate and bis-(3,5-di-tert-butyl-4-hydroxyphenyl) adipate.

4. Hydroxylated thiodiphenyl ethers, for example 2,2'-thiobis(6-tert-butyl-4-methylphenol), 2,2'-thiobis(4-octylphenol), 4,4'-thiobis(6-tert-butyl-3-methylphenol), 4,4'-thiobis(6-tert-butyl-2-methylphenol), 4,4'-thiobis(3,6-di-sec-amylphenol) and 4,4'-bis-(2,6-di-methyl-4-hydroxyphenyl) disulfide.

5. Alkylidene bisphenols, for example 2,2'-methylenebis(6-tert-butyl-4-methylphenol), 2,2'-methylenebis(6-tert-butyl-4-ethylphenol), 2,2'-methylenebis[4-methyl-6-($\alpha$-methylcyclohexyl)phenyl], 2,2'-methylenebis(4-methyl-6-cyclohexylphenol), 2,2'-methylenebis(6-nonyl-4-methylphenol), 2,2'-methylenebis(4,6-di-tert-butylphenol), 2,2'-ethylidenebis(4,6-di-tert-butylphenol), 2,2'-ethylidenebis(6-tert-butyl-4-isobutylphenol), 2,2'-methylenebis[6-($\alpha$-methylbenzyl)-4-nonylphenol], 2,2'-methylenebis[6-($\alpha,\alpha$-dimethylbenzyl)4-nonylphenol], 4,4'-methylenebis(2,6-di-tert-butylphenol), 4,4'-methylenebis(6-tert-butyl-2-methylphenol), 1,1-bis(5-tert-butyl-4-hydroxy-2-methylphenyl)butane, 2,6-bis(3-tert-butyl-5-methyl-2-hydroxybenzyl)-4-methylphenol, 1,1,3-tris(5-tert-butyl-4-hydroxy-2-methylphenyl)butane, 1,1-bis(5-tert-butyl-4-hydroxy-2-methylphenyl)-3-n-dodecylmercaptobutane, ethylene glycol bis[3,3-bis-(3'-tert-butyl-4'-hydroxyphenyl)butyrate], bis(3-tert-butyl-4-hydroxy-5-methylphenyl)dicyclopentadiene, bis[2-(3'-tert-butyl-2'hydroxy-5'-methylbenzyl)-6-tertbutyl-4-methylphenyl] terephthalate, 1,1-bis(3,5-dimethyl-2-hydroxyphenyl)butane, 2,2-bis(3,5-di-tert-butyl-4hydroxyphenyl)propane, 2,2-bis(5-tert-butyl-4-hydroxy-2-methylphenyl)-4-n-dodecylmercaptobutane and 1,1,5,5-tetra(5-tert-butyl-4-hydroxy-2-methylphenyl)pentane.

6. O-, N- and S-Benzyl compounds, for example 3,5,3',5'-tetra-tert-butyl-4,4'-dihydroxydibenzyl ether, octadecyl 4-hydroxy-3,5-dimethylbenzyl-mercaptoacetate, tris(3,5-di-tert-butyl-4-hydroxybenzyl)amine, bis(4-tert-butyl-3-hydroxy-2,6-dimethylbenzyl)-dithioterephthalate, bis(3,5-di-tert-butyl-4-hydroxybenzyl) sulfide and isooctyl 3,5-di-tert-butyl-4-hydroxybenzyl-mercaptoacetate.

7. Hydroxybenzylated malonates, for example dioctadecyl 2,2-bis(3,5-di-tert-butyl-2-hydroxybenzyl)malonate, dioctadecyl 2(3-tert-butyl-4-hydroxy-5-methylbenzyl)malonate, didodecylmercaptoethyl 2,2-bis(3,5-di-tert-butyl-4-hydroxybenzyl)malonate and bis[4-(1,1,3,3-tetramethylbutyl)phenyl] 2,2-bis(3,5-di-tert-butyl-4-hydroxybenzyl)malonate.

8. Aromatic hydroxybenzyl compounds, for example 1,3,5-tris(3,5-di-tert-butyl-4-hydroxybenzyl)-2,4,6-trimethylbenzene, 1,4-bis(3,5-di-tert-butyl-4-hydroxybenzyl)2,3,5,6-tetramethylbenzene and 2,4,6-tris(3,5-di-tert-butyl-4-hydroxybenzyl)phenol.

9. Triazine compounds, for example 2,4-bis(octylmercapto)-6-(3,5-di-tert-butyl-4-hydroxyanilino)-1,3,5-triazine, 2-octylmercapto-4,6-bis(3,5-di-tert-butyl-4-hydroxyanilino)1,3,5-triazine, 2-octylmercapto-4,6-bis(3,5-di-tert-butyl-4-hydroxyphenoxy)- 1,3,5-triazine, 2,4,6-tris(3,5-di-tert-butyl-4-hydroxyphenoxy)-1,2,3-triazine, 1,3,5-tris(3,5-di-tert-butyl-4-hydroxybenzyl) isocyanurate, 1,3,5-tris(4-tert-butyl-3-hydroxy-2,6-dimethylbenzyl) isocyanurate, 2,4,6-tris(3,5-di-tert-butyl-4-hydroxyphenylethyl)- 1,3,5-triazine, 1,3,5-tris(3,5-di-tert-butyl-4-hydroxyphenylpropionyl)hexahydro-1,3,5-triazine and 1,3,5-tris(3,5-dicyclohexyl-4-hydroxybenzyl) isocyanurate.

10. Benzylphosphonates, for example dimethyl 2,5-di-tert-butyl-4-hydroxybenzylphosphonate, diethyl 3,5-di-tert-butyl-4-hydroxybenzylphosphonate, dioctadecyl 3,5-di-tert-butyl-4-hydroxybenzylphosphonate, dioctadecyl 5-tert-butyl-4-hydroxy-3-methylbenzylphosphonate and the calcium salt of monoethyl 3,5-di-tert-butyl-4-hydroxybenzylphosphonate.

11. Acylaminophenols, for example 4-hydroxylauranilide, 4-hydroxystearanilide and octyl N-(3,5-di-tert-butyl-4-hydroxyphenyl)carbamate.

12. Esters of β-(3,5-di-tert-butyl-4-hydroxyphenyl)-propionic acid with mono- or polyhydric alcohols, for example with methanol, ethanol, octadecanol, 1,6-hexanediol, 1,9-nonanedio, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxamide, 3-thiaundecanol, 3-thiapentadecanol, trimethylhexanediol, trimethylolpropane and 4-hydroxymethyl-1-phospha-2,6,7-trioxabicyclo[2.2.2]octane.

13. Esters of β-(5-tert-butyl-4-hydroxy-3-methylphenyl)propionic acid with mono- or polyhydric alcohols, for example with methanol, ethanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxamide, 3-thiaundecanol, 3-thiapentadecanol, trimethylhexanediol, trimethylolpropane and 4-hydroxymethyl-1-phospha-2,6,7-trioxabicyclo-[2.2.2]octane.

14. Esters of β-(3,5-dicyclohexyl-4-hydroxyphenyl)-propionic acid with mono- or polyhydric alcohols, for example with methanol, ethanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis-(hydroxyethyl)oxamide, 3-thiaundecanol, 3-thiapentadecanol, trimethylhexanediol, trimethylolpropane and 4-hydroxymethyl-1-phospha-2,6,7-trioxabicyclo-[2.2.2]-octane.

15. Esters of 3,5-di-tert-butyl-4-hydroxyphenylacetic acid with mono- or polyhydric alcohols, for example with methanol, ethanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxamide, 3-thiaundecanol, 3-thiapentadecanol, trimethylhexanediol, trimethylolpropane and 4-hydroxymethyl- 1-phospha-2,6,7-trioxabicyclo[2.2.2]octane.

16. Amides of β-(3,5-di-tert-butyl-4-hydroxyphenyl)-propionic acid, for example N,N'-bis(3,5-di-tert-butyl-4-hydroxyphenylpropionyl)hexamethylenediamine, N,N'-bis(3,5-di-tert-butyl-4-hydroxyphenylpropionyl)-trimethylenediamine and N,N'-bis(3,5-di-tert-butyl-4-hydroxyphenylpropionyl)hydrazine.

Examples of aminic antioxidants:

N,N'-diisopropyl-p-phenylenediamine, N,N'-di-sec-butyl-p-phenylenediamine, N,N'-bis(1,4-dimethylpentyl)-p-phenylenediamine, N,N'-bis(1-ethyl-3-methylpentyl)-p-phenylenediamine, N,N'-bis(1-methylheptyl)-p-phenylenediamine, N,N'-dicyclohexyl-p-phenylenediamine, N,N'-diphenyl-p-phenylenediamine, N,N'-bis(2-naphthyl)-p-phenylenediamine, N-isopropyl-N'-phenyl-p-phenylenediamine, N-(1,3-dimethylbutyl)-N'-phenyl-p-phenylenediamine, N-(1-methylheptyl)-N'-phenyl-p-phenylenediamine, N-cyclohexyl-N'-phenyl-p-phenylenediamine, 4-(p-toluenesulfamoyl)diphenylamine, N,N'-dimethyl-N,N'-di-sec-butyl-p-phenylenediamine, diphenylamine, N-allyldiphenylamine, 4-isopropoxydiphenylamine, N-phenyl-1-naphthylamine, N-phenyl-2-naphthylamine, octylated diphenylamine, for example p,p'-di-tert-octyldiphenylamine, 4-n-butylaminophenol, 4-butyrylaminophenol, 4-nonanoylaminophenol, 4-dodecanoylaminophenol, 4-octadecanoylaminophenol, bis(4-methoxyphenyl)amine, 2,6-di-tert-butyl-4-dimethylaminomethylphenol, 2,4'-diaminodiphenylmethane, 4,4'-diaminodiphenylmethane, N,N,N',N'-tetra-methyl-4,4'-diaminodiphenylmethane, 1,2-bis[(2-methyl-phenyl)amino]ethane, 1,2-bis(phenylamino)propane, (o-tolyl)biguanide, bis[4-(1',3'-dimethylbutyl)phenyl]amine, tert-octylated N-phenyl-1-naphthylamine, a mixture of mono- and dialkylated tert-butyl/tert-octyldiphenylamines, a mixture of mono- and dialkylated isopropyl/isohexyldiphenylamines, mixtures of mono- and dialkylated tert-butyldiphenylamines, 2,3-dihydro-3,3-di-methyl-4H-1,4-benzothiazine, phenothiazine, N-allylphenothiazine, N,N,N',N'-tetra-phenyl-1,4-diaminobut-2-ene, N,N-bis(2,2,6,6-tetramethylpiperid-4-yl-hexamethylenediamine, bis(2,2,6,6-tetramethylpiperid-4-yl) sebacate, 2,2,6,6-tetramethylpiperidin-4-one and 2,2,6,6-tetramethylpiperidin-4-ol.

Examples of other antioxidants:

Aliphatic or aromatic phosphites, esters of thiodipropionic acid or of thiodiacetic acid, or salts of dithiocarbamic or dithiophosphoric acid, 2,2,12,12-tetramethyl-5,9-dihydroxy-3,7,11-trithiatridecane and 2,2,15,15-tetramethyl-5,12-dihydroxy-3,7,10,14-tetrathiahexadecane.

Examples of metal deactivators, for example for copper, are:

a) Benzotriazoles and derivatives thereof, for example 4- or 5-alkylbenzotriazoles (e.g. tolutriazole) and derivatives thereof, 4,5,6,7-tetrahydrobenzotriazole and 5,5'-methylenebisbenzotriazole; Mannich bases of benzotriazole or tolutriazole, e.g. 1-[bis(2-ethylhexyl)aminomethyl)tolutriazole and 1-[bis(2-ethylhexyl)amino-methyl)benzotriazole; and alkoxyalkylbenzotriazoles such as 1-(nonyloxymethyl)benzotriazole, 1-(1-butoxyethyl)benzotriazole and 1-(1-cyclohexyloxybutyl)tolutraizole.

b) 1,2,4-Triazoles and derivatives thereof, for example 3-alkyl(or aryl)-1,2,4-triazoles, and Mannich bases of 1,2,4-triazoles, such as 1-[bis(2-ethylhexyl)aminomethyl- 1,2,4-triazole; alkoxyalkyl- 1,2,4-triazoles such as 1-(1-butoxyethyl)-1,2,4-triazole; and acylated 3-amino-1,2,4-triazoles.

c) Imidazole derivatives, for example 4,4'-methylenebis(2-undecyl-5-methylimidazole) and bis[(N-methyl)imidazol-2-yl]carbinol octyl ether.

d) Sulfur-containing heterocyclic compounds, for example 2-mercaptobenzothiazole, 2,5-dimercapto-1,3,4-thiadiazole and derivatives thereof; and 3,5-bis[di(2-ethylhexyl)aminomethyl]-1,3,4-thiadiazolin- 2-one.

e) Amino compounds, for example salicylidenepropylenediamine, salicylaminoguanidine and salts thereof.

Examples of rust inhibitors are:

a) Organic acids, their esters, metal salts, amine salts and anhydrides, for example alkyl- and alkenylsuccinic acids and their partial esters with alcohols, diols or hydroxycarboxylic acids, partial amides of alkyl- and alkenylsuccinic acids, 4-nonylphenoxyacetic acid, alkoxy- and alkoxyethoxycarboxylic acids such as dodecyloxyacetic acid, dodecyloxy(ethoxy)acetic acid and the amine salts thereof, and also N-oleoylsarcosine, sorbitan monooleate, lead naphthenate, alkenylsuccinic anhydrides, for example dodecenylsuccinic anhydride, 2-(carboxyethyl)-1-dodecyl-3-methylglycerol and the amine salts thereof.

b) Nitrogen-containing compounds, for example:
  I. Primary, secondary or tertiary aliphatic or cycloaliphatic amines and amine salts of organic and inorganic acids, for example oil-soluble alkylammonium carboxylates, and also 1-[N,N-bis(2-hydroxyethyl)amino]-3-(4-nonylphenoxy)propan-2-ol.
  II. Heterocyclic compounds, for example: substituted imidazolines and oxazolines, and 2-heptadecenyl-1-(2-hydroxyethyl)imidazoline.

c) Phosphorus-containing compounds, for example: Amine salts of phosphoric acid partial esters or phosphonic acid partial esters, and zinc dialkyldithiophosphates.

d) Sulfur-containing compounds, for example: barium dinonylnaphthalenesulfonates, calcium petroleum sulfonates, alkylthio-substituted aliphatic carboxylic acids, esters of aliphatic 2-sulfocarboxylic acids and salts thereof.

e) Glycerol derivatives, for example: glycerol monooleate, 1-(alkylphenoxy)-3-(2-hydroxyethyl)-glycerols, 1-(alkylphenoxy)-3-(2,3-dihydroxypropyl)glycerols and 2-carboxyalkyl-1,3-dialkylglycerols.

Examples of viscosity index improvers are:
Polyacrylates, polymethacrylates, vinylpyrrolidone/methacrylate copolymers, polyvinylpyrrolidones, polybutenes, olefin copolymers, styrene/acrylate copolymers and polyethers.

Examples of pour,point depressants are:
Polymethacrylate and alkylated naphthalene derivatives.

Examples of dispersants/surfactants are:
Polybutenylsuccinic amides or -imides, polybutenylphosphonic acid derivatives and basic magnesium, calcium and barium sulfonates and phenolates.

Examples of antiwear additives are:
Sulfur- and/or phosphorus- and/or halogen-containing compounds, e.g. sulfurised olefins and vegetable oils, zinc dialkyldithiophosphates, alkylated triphenyl phosphates, tritolyl phosphate, tricresyl phosphate, chlorinated paraffins, alkyl and aryl di- and trisulfides, amine salts of mono- and dialkyl phosphates, amine salts of methylphosphonic acid, diethanolaminomethyltolyltriazole, bis(2-ethylhexyl)aminomethyltolyltriazole, derivatives of 2,5-dimercapto-1,3,4-thiadiazole, ethyl 3-[(diisopropoxyphosphinothioyl)thio]propionate, triphenyl thiophosphate (triphenylphosphorothioate), tris(alkylphenyl) phosphorothioate and mixtures thereof (for example tris(isononylphenyl) phosphorothioate), diphenyl monononylphenyl phosphorothioate, isobutylphenyl diphenyl phosphorothioate, the dodecylamine salt of 3-hydroxy-1,3-thiaphosphetane 3-oxide, trithiophosphoric acid 5,5,5-tris[isooctyl 2-acetate], derivatives of 2-mercaptobenzothiazole such as 1-[N,N-bis(2-ethylhexyl)aminomethyl]-2-mercapto-1H-1,3-benzothiazole, and ethoxycarbonyl-5-octyldithiocarbamate.

The compounds of this invention are prepared by methods which are known per se, conveniently in accordance with the following scheme:

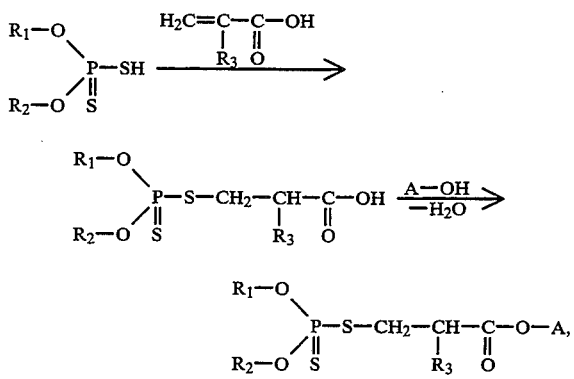

After addition of the dithiophosphoric acid to acrylic acid or methacrylic acid, the resultant substituted carboxylic acid is esterified with an alkohol A-OH by conventional methods, typically by adding para-toluolsulfonic acid or methanesulfonic acid as catalyst and, in some cases, using toluene as entrainer.

A reaction of this kind is exemplified in Example 12.

Alternatively, it is also possible to react esters of dithiophosphoric acid with acrylic acid or methacrylic acid as described, inter alia, in GB 1 569 730.

Specific parameters for carrying out the process embraced by the above reaction scheme can be inferred from the following working Examples. These Examples and the Use Examples illustrate the invention in more detail, but without implying any restriction thereto. Unless otherwise indicated, pans and percentages are by weight.

Example 1: O,O-Diisopropyl-S-2-carboxyethyl dithiophosphate

With stirring, 15.15 g (0.2 mol) of acrylic acid and 0.01 g of hydroquinone are added dropwise at 70° C. to 44.78 g (0.2 mol) of diisopropyl dithiophosphate over 1.5 h. Stirring is then continued for 6 h at 70° C., and the readily volatile constituents are removed under vacuum (70° C./0.02 mbar/0.5 h). Yield: 57.2 g (95%) of a pale yellow liquid $n_D^{20}$:1.5050, $^{31}$P-NMR: 91.4 ppm/H$_3$PO$_4$.

The compounds of Examples 2 to 11 listed in Table 1 are prepared in general accordance with the particulars of this Example 1.

TABLE 1

Compounds of formula
(RO)$_2$P(S)—S—CH$_2$CH$_2$—CO$_2$H

| Example | R | Yield (%) | $n_D^{20}$ | $^{31}$P-NMR ppm/H$_3$PO$_4$ |
|---|---|---|---|---|
| 2 | n-C$_3$H$_7$— | 95 | 1.5090 | 94.8 |
| 3 | i-C$_4$H$_9$— | 97 | 1.5004 | 94.9 |
| 4 | sec-C$_4$H$_9$— | 97 | 1.5020 | 92.3 |
| 5 | i-C$_5$H$_{11}$— | 92 | 1.4989 | 94.6 |
| 6 | cyclohexyl- | 89 | 1.5326 | 91.2 |
| 7 | 2-ethylhexyl- | 95 | 1.4887 | 95.1 |
| 8 | n-C$_{12}$H$_{25}$— | 96 | 1.4876 | 94.9 |
| 9 | C$_{13/15}$H$_{27/31}$— | ≃100 | 1.4864 | 95.0 |
| 10 | C$_8$H$_{17}$—CH(C$_8$H$_{17}$)—CH$_2$— | ≃100 | 1.4826 | 95.3 |
| 11 | C$_9$H$_{19}$-p-phenylene- | ≃100 | 1.5432 | 90.9 |

Example 12: O,O-Diisopropyl-S-2-[carbo-2′,3′-dihydroxypropoxylethyl dithiophosphate A mixture of 57.2 g (0.2 mol) of O,O-diisopropyl-S-2-carboxyethyl dithiophosphate according to Example 1, 18.79 g (0.2 mol) of glycerol, 1.9 g of p-toluenesulfonic acid and 150 ml of toluene is refluxed for 1 h on a water separator. The resultant product is then washed with 50 ml of a 10% solution of sodium sulfate and twice with a 10 % solution of sodium sulfate/5% solution of sodium carbonate and dried over anhydrous sodium sulfate.

The solvent is subsequently removed by distillation on a rotary evaporator and residual solvent is stripped off under vacuum (60° C./0.05 mbar/1 h).

Yield: 64.7 g (90%) of a colourless liquid $n_D^{20}$: 1.5153, $^{31}$P-NMR: 91.3 ppm/H$_3$PO$_4$. The compounds of Examples 13 to 19 listed in Table 2 are prepared in general accordance with the procedure described in Example 12 using the compounds of Examples 7, 3, 8, 9, 5 11 and 1 as ester components.

TABLE 2

Compounds of formula
(RO)$_2$P(S)—S—CH$_2$CH$_2$—CO$_2$—CH$_2$—[CH(OH)]$_n$—CH$_2$OH

| Example | R | n | Yield (%) | $n_D^{20}$ | $^{31}$P-NMR ppm/H$_3$PO$_4$ |
|---|---|---|---|---|---|
| 13 | 2-ethylhexyl | 1 | 95 | 1.5093 | 94.8 |
| 14 | i-C$_4$H$_9$— | 1 | 84 | 1.4941 | 95.3 |
| 15 | n-C$_{12}$H$_{25}$ | 1 | 92 | 1.4906 | 95.2 |
| 16 | C$_{13/15}$H$_{27/31}$ | 1 | 65 | 1.4905 | 96.8 |
| 17 | i-C$_5$H$_{11}$— | 1 | 93 | 1.5073 | 94.9 |
| 18 | C$_9$H$_{19}$-p-phenylene- | 1 | 84 | 1.5402 | 90.5 |
| 19 | i-C$_3$H$_7$ | 0*) | 98 | 1.5073 | 91.2 |

*)An equivalent amount of glycol is used instead of glycerol.

The compounds of Examples 20 to 27 listed in Table 3 are prepared by the process described in Example 12, but replacing glycerol with different alcohols R′OH.

TABLE 3

Compounds of formula
[(CH$_3$)$_2$CH—O]$_2$P(S)—S—CH$_2$CH$_2$—CO$_2$R′

| Example | R′ | Yield (%) | $n_D^{20}$ | $^{31}$P-NMR ppm/H$_3$PO$_4$ |
|---|---|---|---|---|
| 20 | CH$_3$—O—CH$_2$CH$_2$— | 92 | 1.4912 | 91.3 |
| 21 | CH$_3$—O—CH$_2$CH$_2$—O—CH$_2$CH$_2$— | 86 | 1.4912 | 91.2 |
| 22 | n-C$_4$H$_9$—O—CH$_2$CH$_2$— | 93 | 1.4837 | 91.5 |
| 23 | n-C$_4$H$_9$—O—CH$_2$CH$_2$—O—CH$_2$CH$_2$— | 98 | 1.4803 | 91.4 |
| 24 | n-C$_4$H$_9$—O—CO—CH$_2$— | 65 | 1.4844 | 91.0 |
| 25 | CH$_3$—O—CH$_2$—CH(CH$_3$)—O—CH$_2$CH(CH$_3$)— | 83 | 1.4811 | 91.5 |
| 26 | CH$_3$—O—CH$_2$—CH(CH$_3$)—O—CH$_2$—CH(CH$_3$)—O—CH$_2$—CH(CH$_3$)— | 90 | 1.4761 | 91.0 |
| 27 | 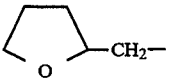 | 83 | 1.5007 | 91.2 |

Example 28: SRV Test

To test the antiwear and friction reducing properties, the novel dithiophosphates are incorporated in an undoped lubricating oil and the coefficient of friction μ is determined at 100° C. and 150° C. using the SRV apparatus (oscillating friction device supplied by Optimol GmbH, Munich; q.v. Lubrication Engineering 39 (11) 1982, Advert. Index cover 3, page 729).

In this method, an oscillating ball (50 Hz) is pressed with a force of 200N against a firmly clamped metal cylinder on which there is a film of test oil. The horizontal and vertical forces are measured with a piezoelectrical transducer. The signal so obtained is transmitted direct to the recorder. At the conclusion of the test, the cross-section of the wear scar on the metal cylinder is measured with a profilometer (TALYSURF 10). The test results are summarised in Table 4.

TABLE 4

| Additive* Example No. | Wear [mm$^2$10$^{-5}$]≠ | | Coefficient of friction μ | |
|---|---|---|---|---|
| | 100° C. | 150° C. | 100° C. | 150° C. |
| — | 85.2 | 217.4 | 0.121 | 0.122 |
| 13 | 16.5 | 37.5 | 0.093 | 0.083 |
| 15 | 13.0 | 61.0 | 0.089 | 0.095 |
| 16 | 28.0 | 52.0 | 0.102 | 0.078 |
| 21 | 58.5 | 84.5 | 0.099 | 0.097 |

*)Additive concentration 2% in mineral oil, viscosity 139.3 mm$^2$s$^{-1}$ at 40° C.
≠)Cross-section of wear scar on the cylinder The low wear index and coefficient of friction relative to the undoped base oil demonstrate that the compounds have antiwear properties.

What is claimed is:

1. A compound of formula I

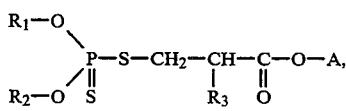

wherein $R_1$ and $R_2$ are each independently of the other $C_3$-$C_{18}$alkyl, $C_5$-$C_{12}$cycloalkyl, $C_5$-$C_6$cycloalkylmethyl, $C_9$-$C_{10}$bicycloalkylmethyl, $C_9$-$C_{10}$tricycloalkylmethyl, phenyl, $C_7$-$C_{24}$alkylphenyl or, taken together, are

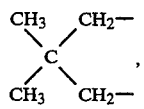

$R_3$ is hydrogen or methyl, A is

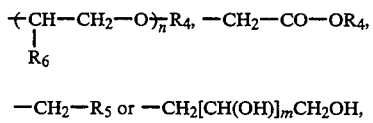

$R_4$ is hydrogen or $C_1$-$C_6$alkyl, and
$R_5$ is a 5- or 6-membered saturated heterocyclic ring,
$R_6$ is hydrogen or methyl,
n is an integer from 1 to 11 and m is an integer from 0 to 4.

2. A compound according to claim 1, wherein $R_1$ and $R_2$ are each independently of the other $C_3$-$C_{18}$alkyl, $C_5$-$C_6$cycloalkyl or $C_7$-$C_{18}$alkylphenyl, $R_5$ is tetrahydrofuryl, n is 1 to 6 and m is 0 to 2.

3. A composition comprising
   a) a lubricant, a machining fluid or hydraulic fluid, and
   b) at least one compound of formula I according to claim 1.

4. A composition according to claim 3, wherein component b) is at least one compound of formula I wherein $R_1$ and $R_2$ are each independently of the other $C_3$-$C_{18}$alkyl, $C_5$-$C_6$cycloalkyl or $C_7$-$C_{18}$alkylphenyl, $R_5$ is tetrahydrofuryl, n is 1 to 6 and m is 0 to 2.

5. A composition according to claim 3, wherein component A) is a lubricant.

6. A composition according to claim 5, wherein the lubricant is an engine oil.

7. A composition according to claim 3, which additionally comprises further stabilisers selected from the group consisting of antioxidants, metal deactivators, further extreme-pressure and antiwear additives and pour-point depressants.

8. A process for enhancing the performance properties of lubricant compositions, hydraulic fluids and machining fluids, which comprises adding thereto at least one compound of formula I as claimed in claim 1.

* * * * *